United States Patent
Engstrand et al.

(10) Patent No.: US 7,505,853 B2
(45) Date of Patent: Mar. 17, 2009

(54) INSPECTION OF COMPOSITE MATERIALS

(75) Inventors: Cody Royce Engstrand, El Cajon, CA (US); Ronald Alan Kline, Ramona, CA (US)

(73) Assignee: San Diego State University Research Foundation, San Diego, CA (US)

( * ) Notice: Subject to any disclaimer, the term of this patent is extended or adjusted under 35 U.S.C. 154(b) by 97 days.

(21) Appl. No.: 11/495,902

(22) Filed: Jul. 27, 2006

(65) Prior Publication Data
US 2007/0044561 A1 Mar. 1, 2007

Related U.S. Application Data

(60) Provisional application No. 60/702,922, filed on Jul. 27, 2005.

(51) Int. Cl.
*G01B 5/30* (2006.01)
(52) U.S. Cl. .............................. 702/39; 702/97; 73/597; 73/598
(58) Field of Classification Search .................. 702/39; 73/598
See application file for complete search history.

(56) References Cited

U.S. PATENT DOCUMENTS 5,955,671 A * 9/1999 Gilmore et al. ............... 73/597
2005/0139006 A1* 6/2005 Lorraine et al. ............... 73/597

* cited by examiner

*Primary Examiner*—Bryan Bui
*Assistant Examiner*—Jonathan Teixeira Moffat
(74) *Attorney, Agent, or Firm*—Morrison & Foerster LLP

(57) ABSTRACT

Since ultrasonic velocities in anisotropic media can change by a factor of 3 or more depending on the direction of propagation, accounting for these changes is extremely important. Also many anisotropic materials are made up of multiple layers of varying orientation, hence the need to account for refraction at ply boundaries. In the present invention, an algorithm is used to calculate these velocities and travel times and properly account for refraction phenomena. Specifically a multilayer SAFT algorithm has been developed that will calculate the time shift, shift and sum A-scan waveforms in layered anisotropic media at any given depth, ply orientation, and number of plies. The algorithm showed an improvement in signal to noise ratio with synthetic data as was expected. This algorithm can be used as a replacement for homogenizing material properties in layered media and will calculate time shifts with increased accuracy since exact material properties are used.

5 Claims, 4 Drawing Sheets

INSPECTION OF COMPOSITE MATERIALS

CROSS REFERENCE TO RELATED APPLICATION

This application claims the benefit of U.S. Provisional application Ser. No. 60/702,922 filed Jul. 27, 2005. The entire disclosure of this prior application is considered to be part of the disclosure of this application and is hereby incorporated by reference herein.

FIELD OF THE INVENTION

The present invention relates to the inspection of composite materials to determine if there are any flaws or defects in the material.

BACKGROUND OF THE INVENTION

Many parts are comprised of composite materials, so it is important to inspect the composite material to find any flaws within the material. The traditional technique of inspecting composite material is to take an ultrasonic transducer, put the transducer over the part and immerse the part in fluid so that there is a means of transmitting the energy from the transducer into the part. To determine if there is a flaw, a wave is propagated through the fluid so that it hits the back surface and reflects back, traveling with the velocity of sound in the material, typically 6000 m/s. Based on this information, it can be determined how much time it will take the wave to travel between the front and back surface. With this information, the gap between the two surfaces can be determined. Once the gap is known, a threshold is set and when signals are detected greater than this threshold, a flaw is present as the signal is reflecting off the flaw and not the back surface. If there is no flaw present in the part, a clean back surface reflection will be seen on an oscilloscope.

The method described above is utilized to inspect various parts made out of composite materials such as the wing of an aircraft. Every spot on the part, in this case an aircraft wing, must be inspected so the transducer scans the part in a serpentine manner. To do this, the transducer is put on a X-Y movable motion controller. Setting the threshold is very important because depending on the size of the threshold, flaws in the composite material can be ignored as small and not causing a problem or included as the flaw will cause a problem. Composite materials are inspected this way as long as the propagating wave is perpendicular to the laminating plies of the composite material regardless of whether the composite is isotropic or anisotropic. Curved composites cannot be inspected this way.

The method described above is a synthetic aperture focusing technique (SAFT) and was originally developed in order to improve the signal to noise ratio and lateral resolution capability in radar applications. Later, this approach was found useful for the same reasons in ultrasonic signal processing. The typical SAFT technique for nondestructive evaluation uses a focused transducer that is scanned over the surface of a part with a series of A-scans (data presentations) recorded in a pulse-echo manner. These A-scans can then be time shifted and summed at each A-scan position at a chosen focal depth to yield enhanced A-scans of the depth. This enhancement is due to constructive interference at a defect and destructive interference of any noise. Although SAFT was originally developed for isotropic materials, it has recently been extended to anisotropic materials; however, it has been limited to unidirectional or homogenized composites.

SAFT in Single Layer Media

The synthetic aperture focus (SAFT) is achieved by time shifting and summing the A-scans surrounding the point of possible defect. A depth is chosen to focus at and the time shifts are computed for the A-scan data at surrounding coordinates. The time shift is computed by taking twice the total distance from the probe coordinates to the focal coordinates divided by the group velocity, v, for the energy-flux direction. The shortest travel time will be when the probe is directly above the focal point, at depth z below, this travel time is given by.

$$T_0 = \frac{2z}{v} \quad (1)$$

As the probe coordinates move in the x-y plane and are no longer directly over the focal point the travel time is given by $$T = \frac{2\sqrt{x^2 + y^2 + z^2}}{v} \quad (2)$$

The time shift that has to be made to the A-scan at any coordinate is then just $$\Delta T = T - T_0 \quad (3)$$

A new A-scan is then saved at that focal point by the summation of all the time shifted A-scans, this summation is given by equation 4 where A is the new A-scan, n is the number of summed waveforms, $A_i$ is the A-scan being summed that is time shifted by $\Delta T$.

$$A = n^{-1} \sum_{i=1}^{n} A_i(\Delta T) \quad (4)$$

This summation is done at all coordinates that A-scans were recorded for any depth that needs to be focused at. Unlike using lenses to focus at a depth in a material, by using the SAFT algorithm, only one scan of the part is needed and the focusing at any chosen depth is done by the algorithm. FIGS. 1 and 2 illustrate the variation in time shifts that are expected in isotropic vs. anisotropic media. FIG. 1 illustrates a time shift for aluminum with a focus depth of 20 in arbitrary units. FIG. 2 is the time shift for a unidirectional graphite-epoxy with fibers oriented with the y-axis focused at a depth of 20 in arbitrary units.

Utilizing SAFT in multilayer media is an extension of SAFT for a single layer. First, it is assumed that there is a perfectly bonded interface between each of the layers in the media. At each layer Snell's law is calculated using the wavenormal and phase velocity of each layer. Starting in the first layer a guess is made that a wavenormal will go directly to the desired focal coordinates in a straight line path and as a result the phase velocity is computed. The desired focal coordinates are determined by guessing where a flaw is in the material. Then using Snell's law, the Christoffel equation, and the global stiffness matrix of each layer, the wavenormal and phase velocity in each layer of the media can be computed. By knowing the wavenormal and phase velocities in every layer, the energy-flux direction and group velocity in each layer can be computed. All of the energy-flux directions are then summed and a determination is made as to if the propagating wave goes to the desired focal coordinates. If the media were isotropic, the correct focal coordinates would be immediately determined without any guess work as group and velocity are the same and there would be no beam skew or refraction due to Snell's law. In an anisotropic media, however, the path would have to be going in a symmetry direction in every layer and the wave velocity would have to stay the same in every layer for the correct focal coordinates to be determined the first time. This is only the situation if the wave is at normal incidence at each layer (i.e. directly above the focal coordinates); therefore the wave is perpendicular to the plane in which the fibers are running in each layer. What is needed is an algorithm utilizing SAFT that can inspect materials with multiple anisotropic layers as commonly used in composite fabrication.

SUMMARY OF THE INVENTION

It is an object of the present invention to provide an algorithm utilizing SAFT that can inspect materials with multiple anisotropic layers as commonly used in composite fabrication.

It is another object of the present invention to account for refraction at ply boundaries of composite materials with multiple anisotropic layers.

In the present invention, an algorithm or process is utilized to inspect materials with multiple anisotropic layers for defects or flaws. In this process, the first step is to determine the known factors or properties of the composite material, such as the ply lay up, the number of plies in the material, the fiber orientation in the plies and the thicknesses of the plies. These properties are generally determined during the manufacturing process and are generally known. Once these properties are known, a stiffness matrix in global coordinates for each ply is computed as well as the common reference using the Christoffel equation. To change from one coordinate system to another, transformation relationships are utilized. The transformed version of the Christoffel matrix elements and the Christoffel tensor perform these calculations. From this the stiffness matrix is determined so it is known how the wave should travel and how the wave travels in the medium can be modeled.

Next, the algorithm makes an initial guess for the wavenormal in the first ply of the material and calculates its phase velocity. An iterative technique is utilized to make the initial guess. The first guess is that the wavenormal is a straight line path even though it is not; it is going to bend at each interface. Once it has been determined where the initial guess is being sent from, the boundary conditions and the reflection and refraction at each of the interfaces is applied and a determination is made where it actually ends up. So next it is figured out how far away this initial guess is from where the wavenormal needs to be, by determining the angular deviation, and the guess is adjusted accordingly.

After the initial guess is made and the wave is analyzed on how it propagates through the material, snell's law is applied for reflection at each interface to compute the new wavenormal and its phase velocity in each layer of the material. This is done until the focus depth is reached. Once the focus depth is reached, the group velocity and direction in each layer is calculated and all the vectors are summed. Next it is determined if the ray path goes to the focus coordinates. If yes, the transit time to the focus coordinates and back is computed and then the algorithm moves to the next probe or focus coordinates and the process begins again at the step where snell's law is utilized to calculate the wavenormal and its phase velocity in each layer below, until the focus depth is reached. If no, the wavenormal is adjusted from the initial guess and its phase velocity is calculated.

BRIEF DESCRIPTION OF THE DRAWINGS

The present invention will be better understood from the following detailed description of an exemplary embodiment of the invention, taken in conjunction with the accompanying drawings in which like reference numerals refer to like parts and in which.

DETAILED DESCRIPTION OF THE DRAWINGS

Since ultrasonic velocities in anisotropic media can change by a factor of 3 or more depending on the direction of propagation, accounting for these changes is extremely important. Also many anisotropic materials are made up of multiple layers of varying orientation, hence the need to account for refraction at ply boundaries. In the present invention, an algorithm is used to calculate these velocities and travel times and properly account for refraction phenomena. Specifically a multilayer SAFT algorithm has been developed that will calculate the time shift, shift and sum A-scan waveforms in layered anisotropic media at any given depth, ply orientation, and number of plies. The algorithm showed an improvement in signal to noise ratio with synthetic data as was expected. This algorithm can be used as a replacement for homogenizing material properties in layered media and will calculate time shifts with increased accuracy since exact material properties are used.

Well-known principles are used in this algorithm such as computing the wave velocity. Wave velocity is computed by an eigenvalue problem governed by the Christoffel tensor. The eigenvalue problem is given as follows: (5) where $\lambda_{il}$ is the Christoffel tensor, $\rho$ is the density, v is the phase velocity, $\delta_{il}$ is the identity tensor, and $\alpha_l$ are components of particle displacement. The Christoffel tenser is given by (6) where $l_k$ and $l_j$ bare components of the wavenormal and $C_{ijkl}$ are components of the stiffness tensor.

$$(\lambda_{il} - \rho^2 \delta_{il}) \alpha i = 0 \tag{5}$$

$$\lambda_{il} = C_{ijkl} l_k l_j \; i,j,k,l = 1,2,3 \tag{6}$$

This eigenvalue problem yields three solutions for the velocity of acoustic wave propagation. The largest solution is of the most interest which is the velocity of the quasilongitudinal wave. The majority of the time, propagating bulk waves are not pure modes (longitudinal or transverse) due to the anisotropy of the material. Pure modes will only propagate in symmetry directions (typically parallel or perpendicular to the reinforcing fibers in a composite).

Figure 1:
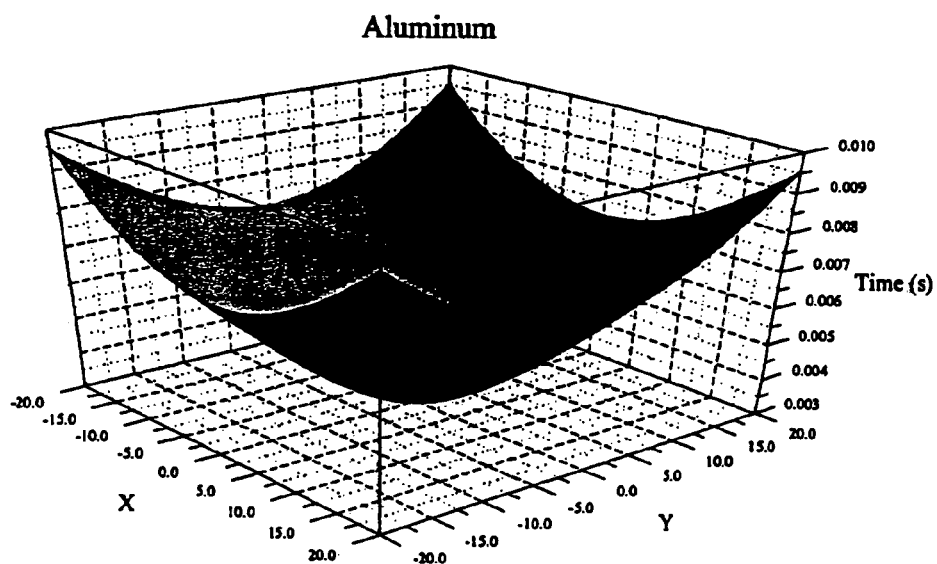
FIG. 1 illustrates a time shift for aluminum with a focus depth of 20 in arbitrary units.
Figure 2:
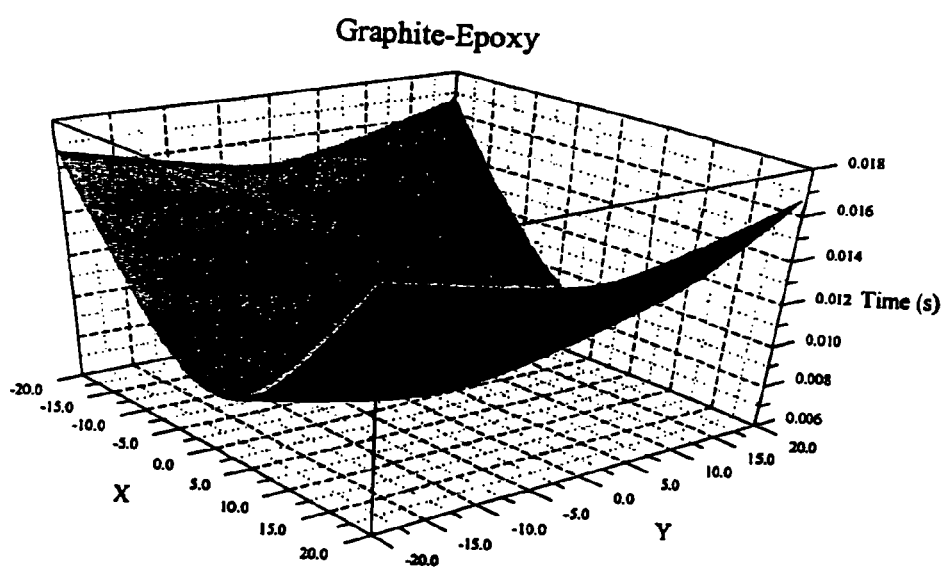
FIG. 2 illustrates a graph showing a time shift for a unidirectional graphite-epoxy with fibers oriented with the y-axis focused at a depth of 20.
Figure 3:
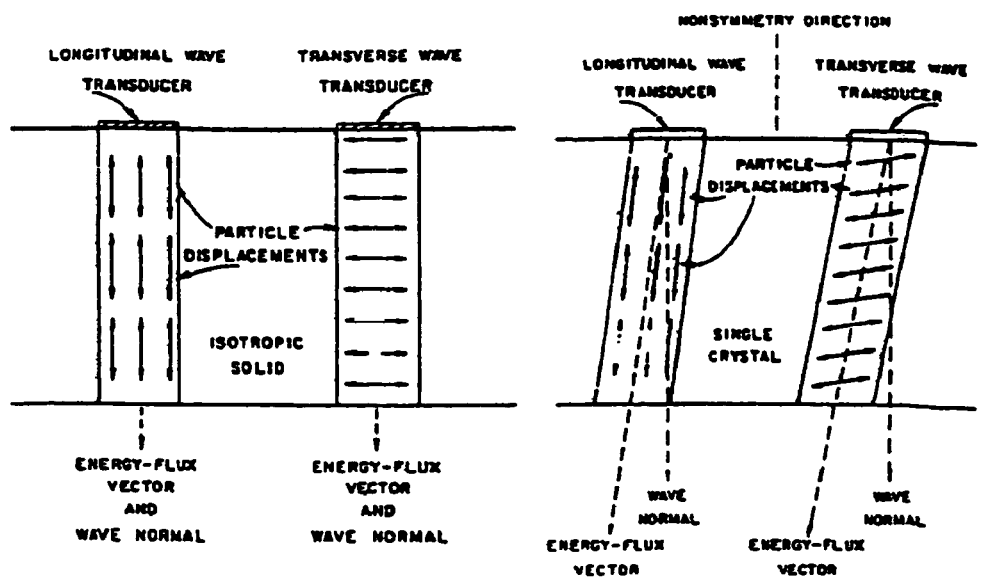
FIG. 3 illustrates the effect of beam skew in an anisotropic material.

The phase velocity of the propagating wave is now determined, however in anisotropic media beam skew takes place if the propagation is not taking place in a symmetry direction. Beam skew is the deviation of the energy away from the wavenormal. The direction of the propagation is known as the energy-flux direction, $S_k$. The effect of beam skew is illustrated in FIG. 3. The group velocity is also different from phase velocity in anisotropic media in nonsymmetry directions. Beam skew (equation #3) and group velocity (equation #4) are governed by the following equations.

$$S_k = \frac{C_{ijkl} l_j a_i a_l}{\rho v_{phase}} \quad (7)$$

$$v_{group} = \sqrt{S_k^2} \quad (8)$$

Figure 4:
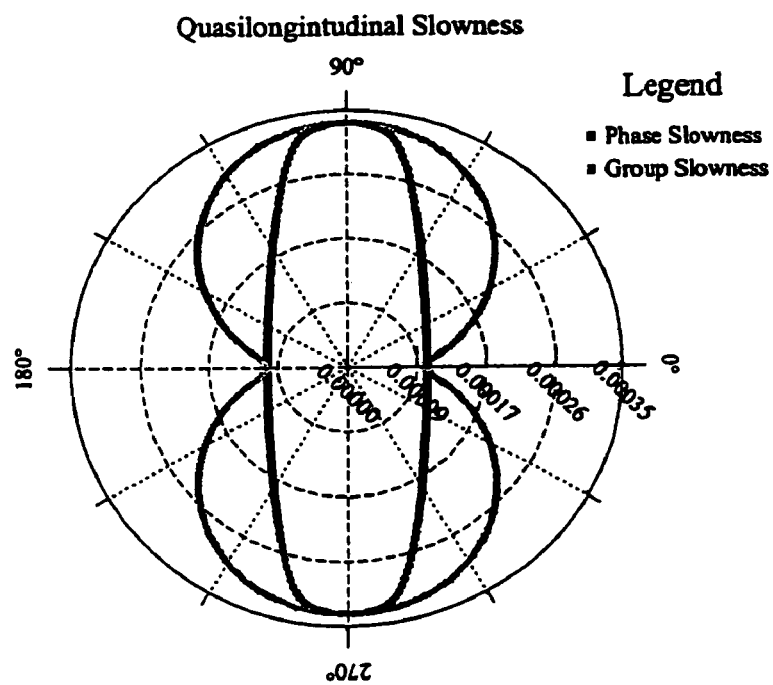
FIG. 4 illustrates a quasilongitudinal slowness curve for graphite-epoxy.

By knowing the components of the stiffness tensor, the energy-flux direction and group velocity of the propagating wave, the time shift can be calculated in the media for any given wavenormal. The group velocity is what will be used to compute the time shift for the SAFT algorithm, with the energy-flux direction, not the wavenormal, being used for the direction of the propagating wave. The difference in group and phase velocity is illustrated in FIG. 4, which shows a quasilongitudinal slowness curve for graphite-epoxy, note that in symmetry directions (0°, 90°, 180°, and 270°) the group and phase slowness are the same.

SAFT in Multilayer Media

SAFT in multilayer media is an extension of SAFT for a single layer. First it is assumed a perfectly bonded interface between the layers. At each layer Snell's law is calculated using the wavenormal and phase velocity. Starting in the first layer, it is guessed that the wavenormal will go directly to the desired focal coordinates in a straight line path and phase velocity will be computed. Then using Snell's law, the Christoffel equation, and the global stiffness matrix of each layer, the wavenormal and phase velocity in each layer of the material is calculated. Now by knowing the wavenormal and phase velocities in every layer, the energy-flux direction and group velocity in each layer of the material is calculated. All of the energy-flux directions are then summed and a check is made to see if the propagating wave goes to the desired focal coordinates.

In an isotropic media, the correct focal coordinates would be determined the first time through, since group and phase velocity are the same and there would be no beam skew or refraction due to Snell's law. In an anisotropic media, the path would have to be going in a symmetry direction in every layer and the wave velocity would have to stay the same in each layer to end up at the correct focal coordinates for the first time. This is only the case if the wave is at normal incidence at each layer (directly above the focal coordinates); therefore the wave is perpendicular to the plane in which the fibers are running in each layer.

For most cases in anisotropic media, the initial guess for the propagating wave does not go to the focal coordinates. A change is then made to the wavenormal in the first ply based on how the projected and actual receiver positions match and everything is computed again. After a number of iterations the correct focal coordinates will be achieved and the travel time is computed by taking twice the distance traveled in each layer, divided by the group velocity in that layer. Those values are then summed for each layer the wave travels through to get to the focus coordinates. New probe or focus coordinates are then chosen and the algorithm is executed again. At each focus depth the set of time shifts only need to be computed once, these same time shifts can be used for all the surrounding points at each point an A-scan was acquired since the spacing of the points at which the scans were acquired are constant. When a new depth of focus is desired the time shifts will need to be computed again since that will cause the initial wavenormal change which in turn will change both phase and group velocities and energy-flux directions.

As discussed previously, for anisotropic media, the initial guess for propagating waves typically does not go to the focal coordinates. After the initial guess, a change is then made to the wavenormal in the first ply of the media based on how the projected and actual receiver positions match and everything is computed again. After a number of iterations the correct focal coordinates will be achieved and the travel time is computed by taking twice the distance traveled in each layer, divided by the group velocity in that layer. Those values are then summed for each layer the wave travels through to get the focus coordinates. New probe or focus coordinates are then chosen and the algorithm is executed again. At each focus depth the set of time shifts only need to be computed once, these same time shifts can be used for all the surrounding points at which the scans acquired are constant. When a new depth of focus is desired the time shifts will need to be computed again since that will cause the initial wavenormal to change which in turn will change both phase and group velocities and energy-flux directions.

Figure 5:
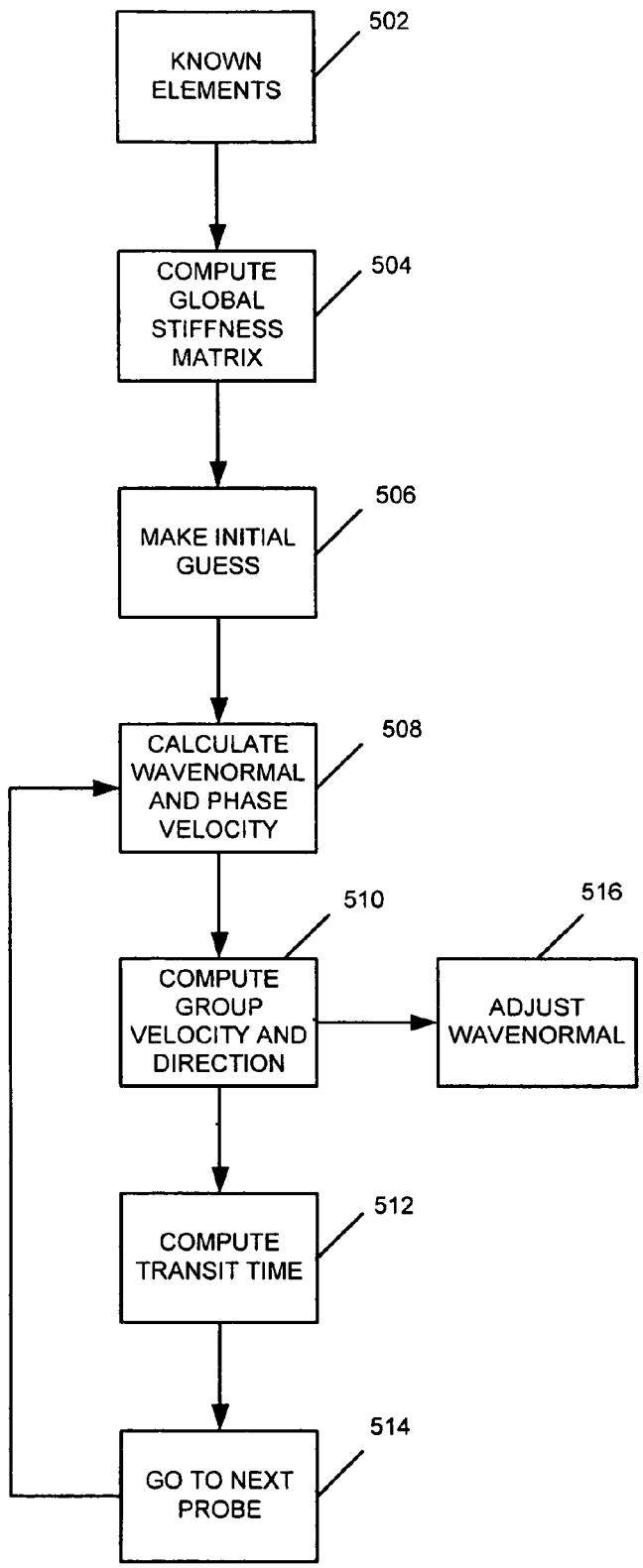
FIG. 5 illustrates a flow chart of the anisotropic multilayer SAFT algorithm.

FIG. 5 illustrates a flow chart of the anisotropic multilayer SAFT algorithm in a preferred embodiment of the present invention. The first step of the algorithm is to determine the known factors or properties about the composite material 502. The known factors or properties are typically the ply lay up, how many plies are in the material, the fiber orientation in plies, the relative thicknesses of the plies, as the plies do not have to be the same thickness, although they usually are, and the material properties, such as what type of graphite epoxy the material is. These properties are typically defined in the manufacturing process. Once these properties are known, a stiffness matrix in global coordinates for each ply is computed 504 because in going from 0 degrees to 45 degrees to 90 degrees, the actual stiffness in material coordinates doesn't change, but because it is skewed relative to the sides of the part, there must be always a common reference point to return to. The common reference is computed using the Christoffel equation, which is described above. To change from one coordinate system to another, transformation relationships are utilized. The transformed version of the Christoffel matrix elements and the Christoffel tensor perform these calculations. From this the stiffness matrix is determined so it is known how the wave should travel and how the wave travels in the medium can be modeled.

Next, the algorithm makes an initial guess 506 for the wavenormal in the first ply of the material and calculates its phase velocity 508. An iterative technique is utilized to make the initial guess. The first guess is that the wavenormal is a straightline path even though it is not, it is going to bend at each interface. Once it has been determined where the initial guess is being sent from, the boundary conditions and the reflection and refraction at each of the interfaces is applied and a determination is made where it actually ends up. So next it is figured out how far away this initial guess is from where the wavenormal needs to be, by determining the angular deviation, and the guess is adjusted accordingly. This is similar to the technique typically utilized for monolithic material, but because reflection and refraction criteria have to be applied to each of the interfaces unlike before, it is more complex.

After the initial guess is made and the wave is analyzed on how it propagates through the material, Snell's law is applied for reflection at each interface to compute the new wavenormal and its phase velocity in each layer of the material. This is done until the focus depth is reached. Once the focus depth is reached, the group velocity and direction in each layer is calculated 510 and all the vectors are summed. Next it is determined if the ray path goes to the focus coordinates. If yes, the transit time to the focus coordinates and back is computed 512 and then the algorithm moves to the next probe or focus coordinates 514 and the process begins again at the step where snell's law is utilized to calculate the wavenormal and its phase velocity in each layer below, until the focus depth is reached. If no, the wavenormal is adjusted 516 from the initial guess and its phase velocity is calculated.

Figure 6:
FIG. 6 illustrates two waveforms, one before any noise was added and then the same waveform with 50% random noise added.
Figure 7:
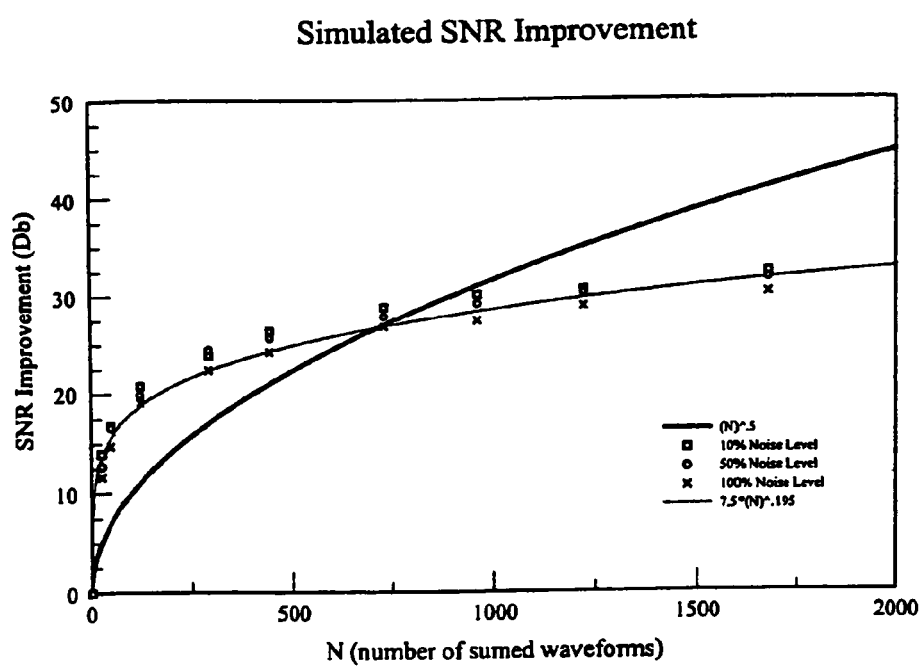
FIG. 7 illustrates the signal to noise improvements in the signals of FIG. 6.

To check the accuracy of the SAFT algorithm, synthetic waveforms were created and random noise was added to them at three levels; 10%, 50%, and 100% (with respect to the maximum amplitude at the defect). The A-scans were then time shifted and summed to check for improvements in the signal to noise ratio. Next, the number of summed waveforms was varied to check the algorithm against the previous works signal to noise ratio improvement. The equation used to calculate signal to noise ratio is given by $$SNR = 20\log_{10}\left(\frac{A - \mu - \sigma}{2\sigma}\right) \quad (9)$$

where A is the maximum amplitude at the defect or flaw, $\mu$ is the background level, and $\sigma$ is the standard deviation around the defect. Turning to FIG. 6, two waveforms are shown, one before any noise was added and then the same waveform with 50% random noise added. FIG. 7 illustrates the signal to noise improvements.

Although an exemplary embodiment of the invention has been described above by way of example only, it will be understood by those skilled in the field that modifications may be made to the disclosed embodiment without departing from the scope of the invention, which is defined by the appended claims.

We claim:

1. A method for analysis or inspection of a multi-ply composite material with anisotropic layers comprising:
   (a) determining properties of the multi-ply composite material,
   wherein the properties comprise the ply lay up, the number of plies in the material, the fiber orientation in the plies and/or the thicknesses of the plies;
   (b) computing a stiffness matrix in global coordinates for each ply in the multi-ply composite material using a Christoffel equation, and changing from one coordinate system to another using calculations based on a transformed version of Christoffel matrix elements and a Christoffel tensor, and using the stiffness matrix to determine how a wave should travel and how the wave travels in the material;
   (c) computing a common reference using an algorithm comprising a Christoffel equation;
   (d) making an initial guess of an ultrasonic wavenormal in the first ply of the composite material and calculating wave phase velocity by assuming that the wavenormal is a straightline path even though the wavenormal actually bends at each interface;
   (e) determining the angular deviation of the first guess wavenormal from an actual ultrasonic wavenormal by determining how far away the initial guess of step (d) is from the actual wavenormal by (1) determining the actual ultrasonic wavenormal by determining where the initial guess of the wavenormal in the first ply is being sent from, applying the boundary conditions and the reflection and refraction at each of the ply interfaces, and determining where the ultrasonic wavenormal actually ends up; (2) determining how far away the initial guess of step (d) is from where the actual ultrasonic wavenormal as determined in (e)(1) by determining the angular deviation;
   (f) adjusting the initial guess wavenormal of step (d) using the angular deviation determination of step( e);
   (g) computing a new wavenormal and its phase velocity by applying Snell's law for reflection at each interface in the composite material to compute the new wavenormal and its phase velocity in each ply layer of the multi-ply composite material until the focus depth is reached;
   (h) calculating the group velocity and direction in each layer and summing all the vectors;
   (i) determining if the ray path of the ultrasonic wave goes to the focus depth coordinates; and
   (j)(1) if the ray path of the ultrasonic wave does go to the focus depth, the transit time to the focus coordinates and back is computed and the method comprises a further step comprising moving the to the next probe or focus coordinates and repeating (iterating) the method at step (g) where Snell's law is utilized to calculate the wavenormal and its phase velocity in each layer below, until the focus depth is reached; or
   (2) if the ray path of the ultrasonic wave does not go to the focus depth, the wavenormal is adjusted from the initial guess and its phase velocity is calculated and stored and/or presented to a user.

2. The method of claim 1, wherein the known properties of the composite material comprise the ply lay up, the number of plies in the composite material, the fiber orientation in the plies and the relative thickness of the plies.

3. The method of claim 1, wherein the multi-ply composite material is a composite fabrication material.

4. The method of claim 3, wherein the composite fabrication material comprises a graphite-epoxy material.

5. The method of claim 1, wherein the calculated phase velocity is used to determine if there are any flaws or defects in the material.

* * * * *